United States Patent [19]

Mealy et al.

[11] Patent Number: 5,605,317
[45] Date of Patent: Feb. 25, 1997

[54] ELECTRO-MAGNETICALLY OPERATED VALVE

[75] Inventors: Stephen Mealy, Sagamore Beach; Keith D. Besse, Falmouth, both of Mass.

[73] Assignee: Sapphire Engineering, Inc., Pocasset, Mass.

[21] Appl. No.: 315,943

[22] Filed: Sep. 30, 1994

Related U.S. Application Data

[63] Continuation-in-part of Ser. No. 215,505, Mar. 21, 1994.

[51] Int. Cl.[6] .............................. F16K 31/06; F04B 7/00
[52] U.S. Cl. .............................. 251/129.01; 251/129.15; 251/129.21; 417/505
[58] Field of Search .................. 251/129.21, 129.15, 251/129.01; 417/505

[56] References Cited

U.S. PATENT DOCUMENTS 3,984,315 10/1976 Ernst et al. .
4,103,686 8/1978 LeFevre .
4,420,393 12/1983 Smith .
4,790,351 12/1988 Kervagoret ............... 251/129.21 X
4,911,405 3/1990 Weissgerber .

*Primary Examiner*—Kevin Lee
*Attorney, Agent, or Firm*—Thomas A. Kahrl, Esq.

[57] ABSTRACT

An electro-magnetically operated valve for control of pressurized fluid including a coil bobbin disposed within a housing, having a plunger subassembly moveably mounted in said housing having a fixed valve seat at one end and a magnet mounted at the opposite end and including a flow passage extending there between, whereby the plunger is moveable responsive to an electronic coil mounted in the coil bobbin between an open position wherein the valve body member is in spaced relationship with the valve seat permitting flow of pressurized fluid, and a closed position whereby the valve body member is seated against the valve seat, said valve being connected to sensor apparatus for sensing phase relations of a piston of a pump operationally connected to a switch apparatus for forming a magnetic circuit including the electro-magnetic coil such that the valve is operated by positively controlling the opening the opening and closing of the valve by passing a current through the coil.

14 Claims, 14 Drawing Sheets

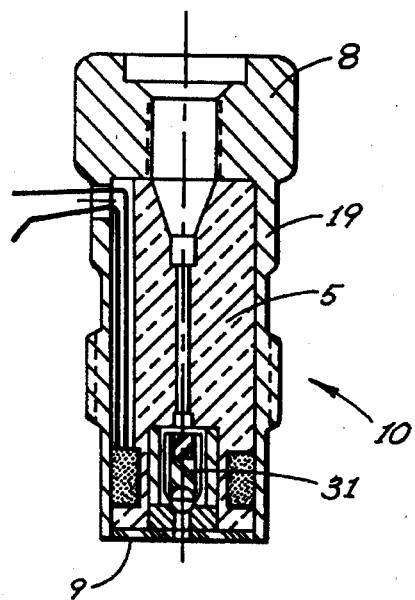
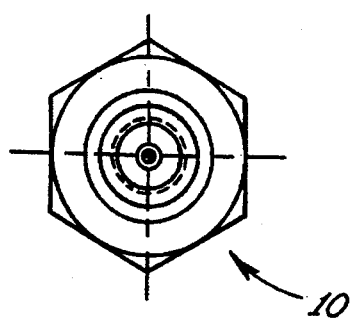
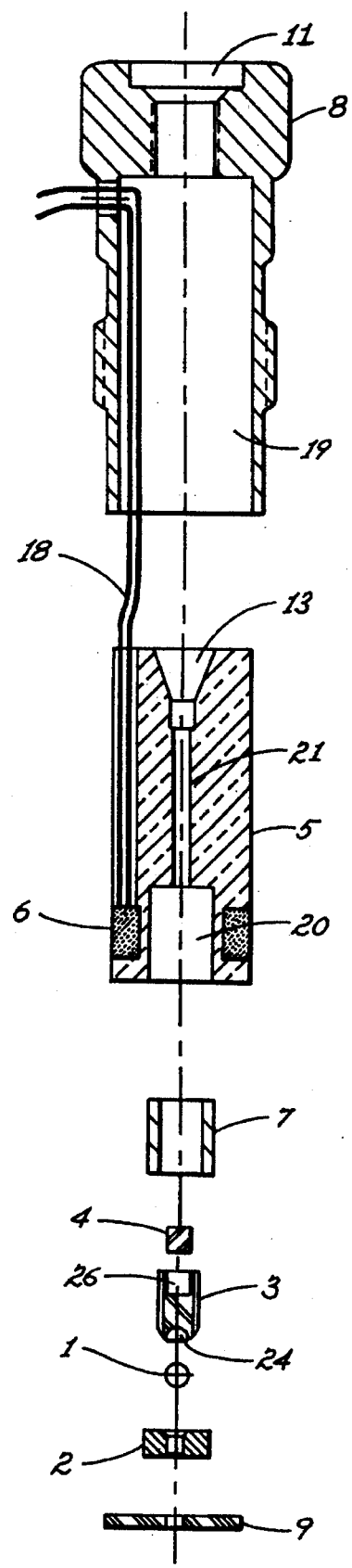
FIG. 1
FIG. 2
FIG. 3

CURRENT SUPPLY

ELECTRO-MAGNETICALLY OPERATED VALVE

REFERENCE TO PRIOR APPLICATIONS

This application is a continuation-in-part of U.S. patent application Ser. No. 08/215,505 filed Mar. 21, 1994, entitled ELECTRO-MAGNETICALLY OPERATED VALVE hereby incorporated by reference in its entirety. In the original, parent application an electro-magnetically operated valve is disclosed which operates both as a check valve and as a normal open-close valve (as opposed to a one-way check valve) as long as maximum liquid pressure can be overcome by the electro-magnetic force of the valve acting against the valve's seat for controlling the flow of pressurized fluid, as is set forth in FIGS. 1–12.

BACKGROUND OF THE INVENTION

In applications such as high performance liquid chromatography (HPLC), capillary electrophoresis (CE) and mass spectrometry (MS) it is important that reagents and samples flow continuously and precisely without pulsations and other flow irregularities. The current trend, largely driven by the rising cost of consumables and the rising cost of environmentally responsible disposal of used chemicals, is to develop methods that require much lower flow rates than were previously common. Piston pumps that rely on one-way check valves have been the preferred mechanism for liquid delivery because they can provide continuous flows (as opposed to a syringe pump which must be refilled occasionally) and are cost effective and reliable.

Applicant is aware of prior art devices employing one-way check valve with magnets. In particular, LeFEVRE U.S. Pat. No. 4,103,686 shows a steel ball, a plunger and an electromagnet. Here the plunger moves the ball into a retracted position and the ball returns to its seat by the action of gravity and fluid pressure. ERNST ET AL. U.S. Pat. No. 3,984,315 shows a spring loaded suction valve and delivery valve in a chromatography pump; see also SMITH U.S. Pat. No. 4,420,393.

In another patent to WEISSGERBER U.S. Pat. No. 4,911,405 there is shown a valve unit for use at the suction inlet of a pump having a spring loaded ball an armature of a solenoid to lift a pin to lift the ball to control the flow of the pump. See also SMITH, U.S. Pat. No. 4,420,393.

However, one-way check valve devices disclosed by the prior art become problematic at flow rates because the ball, used as the valve body of such a one way check valve, often does not fully lift off the seat during the "open check valve" portion of pump operation, typically the piston stroke, and because a positive seal is difficult to maintain during the sequence of the "check valve closed" portion of the piston stroke, thereby resulting in pulsations and other flow irregularities. These collective difficulties are generally believed to be a result of lower pressures and slower piston speeds inside a pump chamber which combine to cause timing and flow variations in check valves used in these systems.

Currently available ball and conical seat one way check valves rely on liquid pressure, and to some extent on gravity, to move between an open position and a closed position. At low flow rates and pressures (e.g. 1 microliter per minute and 2000 pounds per square inch) pressure/gravity actuation becomes questionable in that the ball typically only partially rise above the conical seat during the well recognized "check valve open" portion of a pump piston stroke and does not make a good seal during the "check valve closed" portion of a piston stroke of an associated pump. Furthermore, during this "check valve open" portion of a piston stroke, the ball can remain in point contact with the conical seat and result in asymmetrical flow around the ball. These and other related phenomena can result in pulsations and flow irregularities that can adversely affect measurements made by the respective system employed such as a high performance liquid chromatography (HPLC) system or a mass spectrometry (MS) system receiving pressurized fluid being fed by such a pump.

It is therefore desirable to provide for a new and improved electromagnetically operated valve for control of pressurized fluid adapted to provide positive control over the position of a valve body in both directions i.e., to open said valve and to close said valve which overcomes at least some of the disadvantages of the prior art.

SUMMARY OF THE INVENTION

The parent application is directed an electro-magnetically operated valve used to control flow of pressurized fluid, typically provided by a system employing one or more piston pumps. Said valve includes a magnetically operated ball valve operable between an open and closed position having an actuation device, typically a switching device, to provide positive control over the position of a moveable valve body relative to a fixed valve seat. Positive control is provided by toggling the actuation device whereby the moveable valve body includes a magnet which is pushed or pulled by current flowing through a nearby coil contained in a coil bobbin wherein a timed relationship between valve opening or closing can be precisely controlled. In the original invention, control is achieved by relating the timing relationship between valve opening and valve closing and piston stroke position such that the ball can be actively forced against a fixed valve seat to affect a positive seal or pulled away from such seat to affect a positive and consistently reproducible open flow condition with a consistent amount of resistance thereby reducing unwanted variability and pulsations as well as improving flow stability.

The original invention is directed to applications such as high performance liquid chromatography (HPLC), capillary electrophoresis (CE) and mass spectrometry (MS), where it is important that reagents and fluid samples flow continuously, precisely and with minimum pulsations. One or more piston pumps have been the preferred mechanism, because they can provide continuous flows and are cost effective.

In the parent invention the electro-magnetically operated valve (EMACV) includes a housing having a conical inlet aperture for receiving pressurized fluid from a piston pump apparatus, having two piston elements arranged such that at least one is providing positive flow at all times. Said housing having a central chamber including a coil bobbin, a fluid conduit extending axially between said inlet aperture and an outlet for passage of pressurized fluid.

A fixed valve seat is positioned in said housing having a substantially conical inner surface constructed of nonmagnetic material adapted to co-operate with the valve body sealing member. The valve body sealing member is positioned in a plunger subassembly cage disposed coaxially in the tubular chamber. The moveable plunger is disposed coaxially including a valve body seal member at one end of said plunger and having a magnet mounted at the other end. Operationally the plunger and associated valve body seal member is moveable responsive to electro-magnetic means mounted in said valve, wherein movement is between an open position wherein the valve body member is in spaced relationship with the conical surface of the seat permitting flow of fluid around and through said conduit and a closed position whereby the body sealing member is seated on said conical seat.

In operation, the electro-magnetically actuated valve device of the present invention further is arranged to move a valve body consisting of a ball in two directions with the first direction being toward a first position and a second position, typically the first being an inlet, open position and the second being an outlet, closed position. A magnetic circuit is formed by toggling the actuation device such as a toggle switch, whereby said valve is operated by passing a current through the coil of wire to produce a magnetic field. In this condition the open or closed state of said valve is determined by the direction of current flow through said coil. The current which acts on the magnet contained in the plunger cage alternatively a) urges the ball formed of nonmetallic material against an associated seat for sealing said valve's outlet or b) urges the ball away from the seat to open it.

This invention can also serve as a normal open-close valve (as opposed to a one-way check valve) as long as maximum liquid pressure can be overcome by the electro-magnetic force pushing the magnet ball assembly against the seat.

Summary of Changes

In the present invention, a low pressure seal was added to increase sealing performance as we found a separate seal with a lower durometer required less compression to seal the leak path of the valve. In this preferred embodiment, said low pressure seal is constructed of an "o" ring. Also in this embodiment of the present invention a flow passage is formed in the plunger to insure that flow is not restricted. In this embodiment an optical sensor, typically an optical encoder has replaced the cam follower and micro switch of the parent application. Also it is now apparent that currently all pumps in the art having computer controls, commonly known as "PC-ready" pumps are using a conventional stepper motor being operated using an optical encoder to "find" the surface of an associated cam. Such a cam is shaped to indicate piston stroke position, and therefor the optical encoder "finds" and signals the piston position of one or more piston pumps employed in a given system for providing a continuous flow of fluid. The same sensors are also employed to time the operation of actuating devices for electromagnetically moving the plunger subassembly in the current invention from a first position to a second position, new parts have been added to the valve of the present invention including an upper seal plate 117, a locking pin 116, a lower seal plate 109, an improved bobbin 105 and a low pressure seal 115.

As an example of the improvements noted, tests were conducted on an HPLC pump, an Thermal Separation Products/LDC Model CM4100 Pump, Serial Number 048556 using the manufacturer's standard check valves and then substituting two EMACV valves on the inlet side of the two pump heads of the Pump. This pump was chosen as it is a good example of the type of pump currently available in the art and can be readily interfaced with the EMACV valves as shown in FIG. 11. FIG. 24 shows the improvements of the pressure measured at the pump's pressure transducer for three different flow rates (1.0 mL/minute, 0.5 mL/minute and 9.1 mL/minute) using water as a medium. The left side of the trace is the standard inlet check valves; the right side of the trace shows the improvements made when an EMACV Inlet valve is substituted and the coil energized.

Another application for the present invention has been found for mixing of solvents. HPLC pumps are often equipped with input proportioniong valves, typically four. These input proportioning valves are opened sequentially during each suction stroke of the pump. The total duration of the open time per suction stroke for each proportioning valve is controlled by a microprocessor to provide the desired mixture of reagent. When the mixture varies as a function of time the pump is said to deliver a reagent gradient. These gradients are generally used to separate in time the elutions from a column for detection and/or collection (purification).

Currently as practiced in the art, this type of metering of said solvents is accomplished by four Teflon diaphragm solenoid valves which feed said solvents into a standard inlet check valve positioned on a pump head. These Teflon valves all operate at low pressures below 100 PSI.

Applicant has discovered that the present invention EMACV can replace these Teflon valves because now said EMACV can be controlled as to the amount of time it is opened and closed. It is possible to mount 4 EMACV valves directly into a manifold or directly to a pump head itself which will serve not only as an inlet check valves, but also as a gradient proportioning valves. Further, it is discovered that multiple operation of the valves will improve mixing and can in some applications eliminate the need for a mixing chamber following the pump as is now required.

FIG. 23 shows the typical set-up prior art for proportioning using a four-valve manifold attached in line to the pump head. The figure shows four conventional solenoid-operated valves mounted to a rectangular manifold, with four inlets. These would typically lead from the four solvents being used in the gradient proportioning.

The outlet of this manifold leads to a mixing chamber shown as a cylinder, entry at base, exit out the top of the page. This insures the "slugs" of the four solvents are thoroughly mixed prior to being drawing into the pump head. From the first pump head a line leads to the second pump head and finally out the outlet check valve (top of the right-hand pump head).

FIG. 24 shows a pump head with four EMACV's of the present invention installed radially about a pumphead. Again, the four solvents are drawn into the pumphead through the four EMACV's, each administering the required volume of each of the solvents. The pumphead acts as a mixing chamber, eliminating the pre-mixing required using the manifold valving shown in FIG. 23. The balance of the figure is the same as FIG. 23.

The invention will be described for the purposes of illustration only in connection with certain embodiments. However, it is recognized that those persons skilled in the art may make various changes, modifications, improvements and additions on the illustrated embodiments all without departing from the spirit and scope of the invention.

BRIEF DESCRIPTION OF THE DRAWINGS

FIG. 1 is a cross-sectional view of an electro-magnetically actuated valve according to the original invention, shown in an outlet valve arrangement.

FIG. 2 is an end view of the electro-magnetic actuated valve of FIG. 1.

FIG. 3 is a exploded cross sectional view of the electro-magnetically actuated valve of FIG. 1.

DETAILED DESCRIPTION OF THE PREFERRED EMBODIMENT

Figure 4:
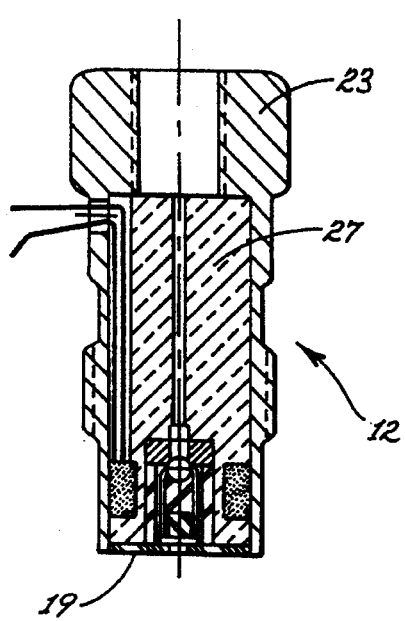
FIG. 4 is a cross sectional view of the electro-magnetically actuated valve of FIG. 1 shown in the inlet arrangement.
Figure 4:
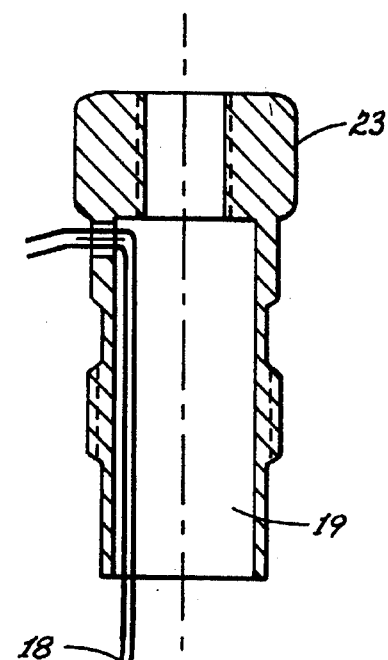
Figure 5:
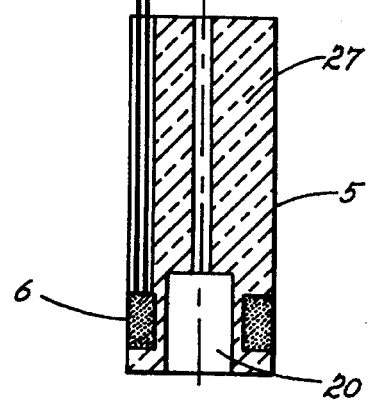
FIG. 5 is an exploded cross sectional view of the electro-magnetically actuated valve of FIG. 4.
Figure 5:
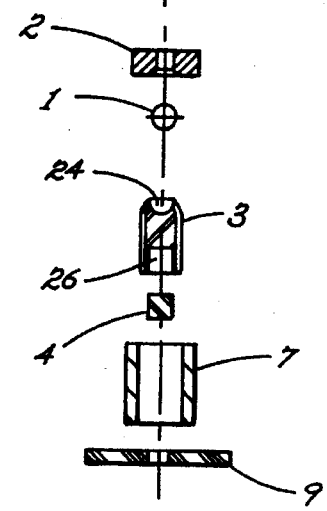

With reference to FIGS. 1–12 of the parent application, there is shown an electro-magnetically actuated valve shown in FIG. 1 as an outlet valve (10) and shown in FIG. 4 as an inlet valve (12). In particular outlet valve (10) includes a housing (8) having an inlet (11) at one end and a hollow cylinder (19) at another opposite end. A coil bobbin (5) is positioned in said hollow cylinder having an inlet (13) at one end and a tubular chamber (20) at the other end including a fluid conduit (21) extending between said inlet and said tubular chamber.

Figure 6:
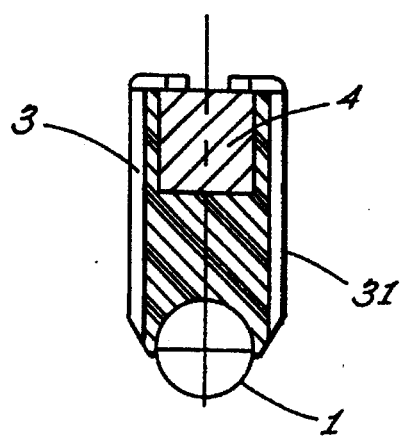
FIG. 6 is a cross sectional view of the plunger assembly of the electro-magnetically actuated valve of FIG. 1.
Figure 7:
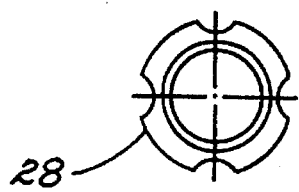
FIG. 7 is an end view of the plunger assembly of FIG. 6 showing longitudinal flow channels.

In the parent application as is shown in FIG. 6, a plunger subassembly (31), is mounted in tubular chamber (20) and includes a plunger cage (3) disposed coaxially in said tubular chamber (20), a sleeve member (7) configured to enclose said plunger cage, a fixed valve seat (2) adapted to associate with a valve body member, consisting of a ball (1) mounted in a concave carrier (24) at one end of plunger cage (3). As is shown in FIG. 7, longitudinal sleeve channels (28) are provided in said plunger cage including by-pass slots (30) at an inlet end thereof, see FIGS. 7 & 8. As is shown in FIG. 3, ball (1) is mounted at one end of plunger cage (3) and at an opposite end thereof, a magnet (4) is mounted in a recess (26). A sealing washer plate (9) is provided at a distal end of housing (8) for enclosing tubular chamber (20) and sealing the outlet of the plunger sub-assembly 31.

In this embodiment a coil (6) is provided in the coil bobbin (50) mounted in a recess adjacent tubular chamber (20) and is connected by a plurality of leads (18) which are connected to conventional switching apparatus not shown. Said coil is magnetically linked to magnet (4) whereby a magnetic circuit is formed including the moveable plunger cage (3) including said magnet and ball (1). Once a magnetic circuit is formed, said valve is operated for positively controlling the opening and closing by passing a current through the coil of wire to produce a magnetic field. In this condition the open or closed state of said valve is determined by the direction of current flow through said coil, which acts said magnet urging said ball formed of nonmetallic material against an associated seat for sealing said valve's outlet.

Figure 8:
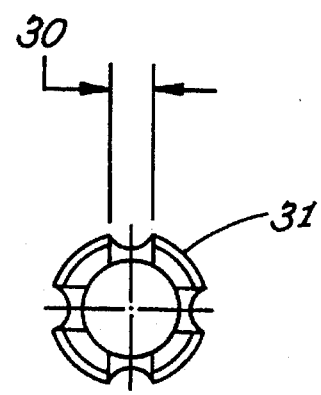
FIG. 8 is an end view of an outlet end of the plunger assembly showing the by-pass slots.

In this embodiment, as is shown in FIGS. 6, 7, & 8, plunger cage (7) is grooved to provide enhanced flow including grooves (28) along its entire length with grooves (28) and it includes transverse bypass slots (30) positioned across an inlet face as is shown in said figs. so that liquid passing through said valve can continue to flow through even though plunger cage (7) is forced up against coil bobbin (5). The position of coil (6) is selected so as to adequately magnetically influence magnet (4).

It is noted, as is shown in FIG. 4, seat (12), ball (1), plunger (3), magnet (4) and plunger cage subassembly (7) may be assembled in reverse order in housing 23 and coil bobbin 27 for inlet check valve (12). A particular advantageous feature of said valve is that all of the components are readily disassembled or alternatively assembled into housing (8) and sealed in place by sealing washer (9). In this embodiment when installed in a piston pump, the internal parts of plunger subassembly (31) are in compression to seal against internal leaks. Furthermore sleeve (7) may be readily removed from said housing for cleaning and replacement of parts of valve elements contained therein. Referring to FIG. 7, longitudinal groove (28) and radial bypass grooves (30) are chosen to be large enough so as not to restrict flow through said valve. In this embodiment of the invention, flow restriction is determined by the inside diameter of associated system tubing not said bypass grooves in said plunger nor spacing between ball (1) and associated seat (2).

Figure 10:
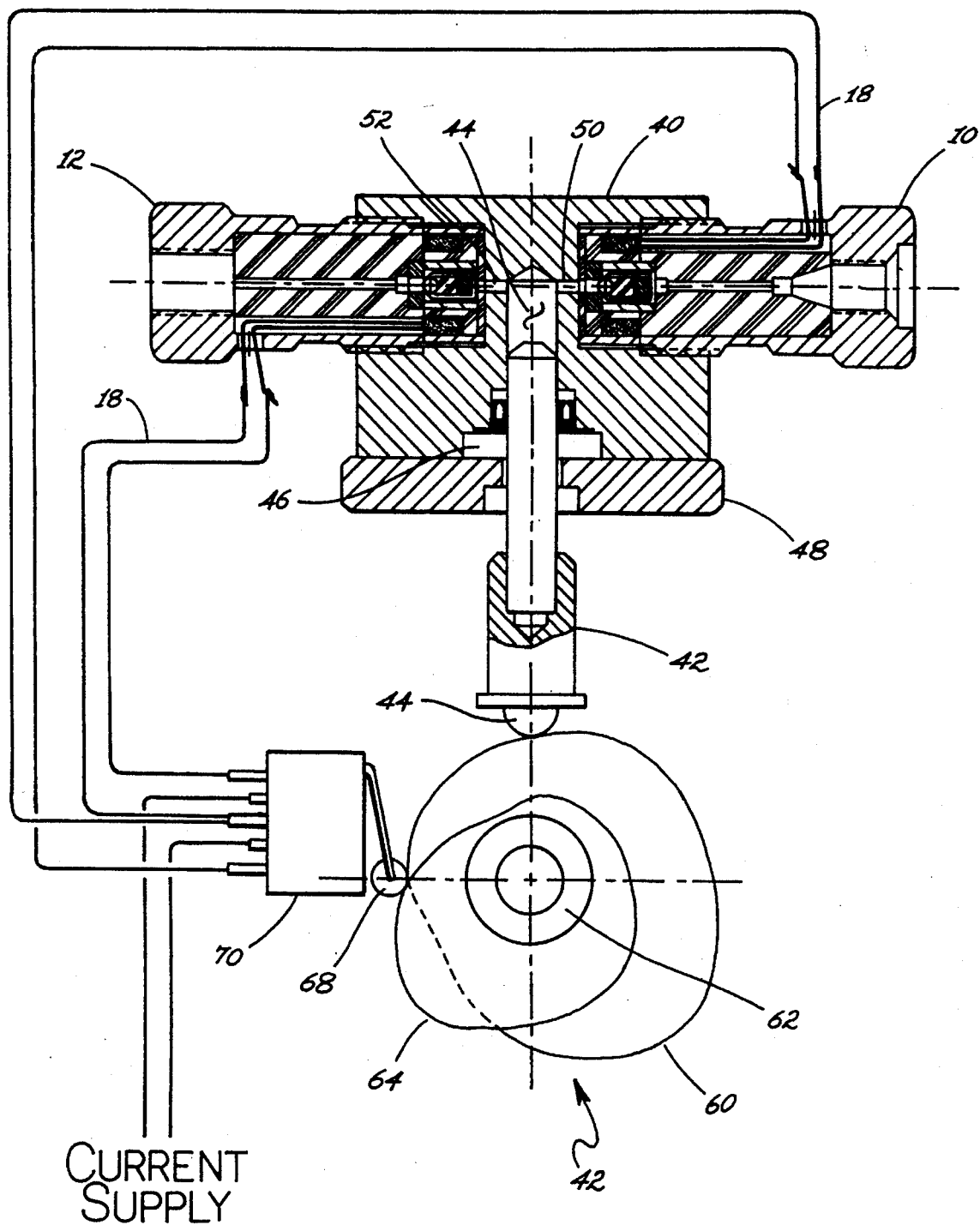
FIG. 10 shows an electro-magnetically operated fluid control system showing a cross section employing an outlet valve and an inlet valve mounted in a pump body including a CAM operated control system.

Referring to FIG. 10, there is shown a electro-magnetically operated fluid control system employing both an outlet valve configuration (10) and an inlet valve configuration (12) mounted in a pump body. FIG. 10 showing an outlet configured valve (10) and an inlet configured (12) valve mounted on a pump body (40) including a cam operated control system (42). Said pump body includes a cylinder (44) including a piston assembly (42) having a cam follower (44) and a piston seal (46) contained by a pump mount plate (48). As is shown in FIG. 10, outlet valve is mounted in an opposed position to inlet valve (12) being a connected by interconnect channels (50 and 52) in communication with said cylinder. Cam operated control system (42) includes a pump cam (60) which cooperates with pump follower (44) mounted on a drive shaft (62) and a switch cam (64) also mounted on said drive shaft in association with a switch follower (68) connected to an electrical switch (70).

Figure 9:
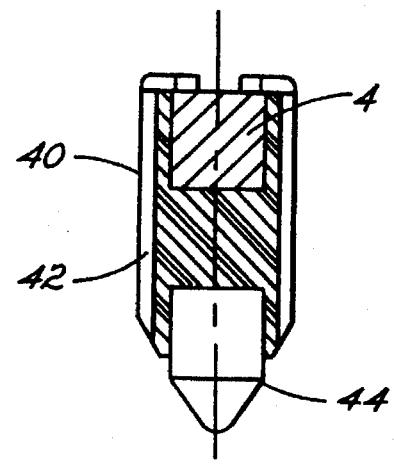
FIG. 9 illustrates an alternate embodiment of a plunger assembly of the electro-magnetically actuated valve of the present invention showing a conical body element and associated seat.
Figure 9:
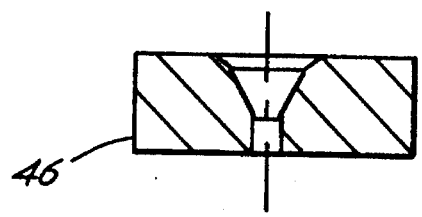

An alternate embodiment of a plunger assembly shown at 40 in FIG. 9 includes a conical valve body 44 contained in plunger 42 adapted to associate with valve seat 46 having a conical valve seat.

Referring to FIG. 10, typical pumps utilize two pistons arranged such that at least one is providing positive flow at all times. For example, two identical piston and chamber assemblies operated with identical strokes but 180° out of phase creates parallel flow. Alternately, it is possible to operate two identical piston and chamber assemblies in series as a master/slave configuration. In this series arrangement piston strokes will be different, the pushing stroke of the master piston provides flow to a load and flow to fill the slave. During a pulling stroke of the master piston, the slave piston pushed to sustain the flow load. Other configurations are possible and intended to within the scope of the present invention.

In actual operation pulsations can be reduced by leading or lagging the electro-magnetically actuated valve toggle points relative to respective piston reversal points. For example, an outlet configuration (10) valve should remain closed until the pressure inside tubular chamber (20) equals the pressure inside the line feeding a load. In this case valve opening lags the piston reversal point. Generally, inlet interval will be shorter than outlet interval to maintain constant flow without pulsation.

Referring to FIG. 10, in typical operation with a piston pump, the electro-magnetically actuated check valves will have current flowing through each respective coil (6) at all times during pumping action. The direction of current flow through said coils will reverse to change said valve condition from open to closed. Since magnetic flux depends on current not voltage, it will generally be better to regulate current in coil (6). The suggested implementation of a double pole double throw (DPDT) switch is with a solid state (transistor based) device although a simple relay will work for many applications when switching speed is on the order of 1 Hertz or less.

Figure 12:
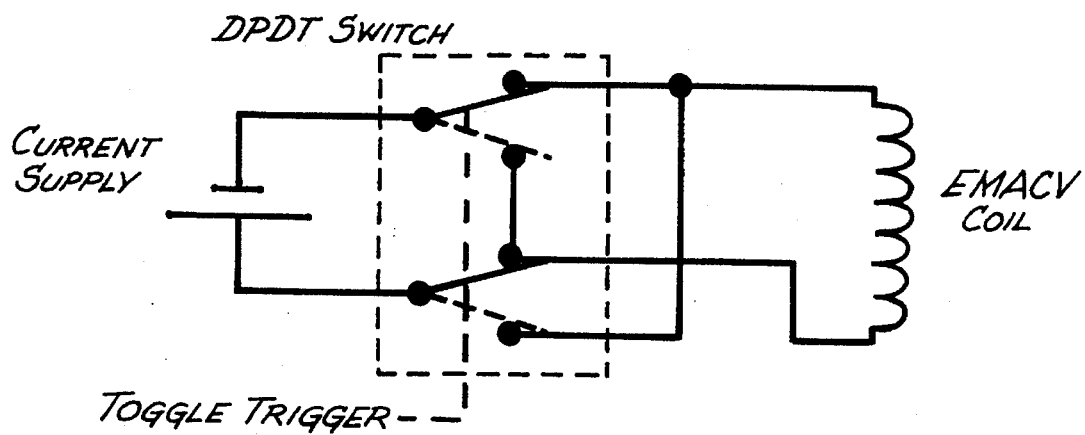
FIG. 12 illustrates a very basic circuit for actuation including opening and closing of the electro-magnetically operated valve of the original invention.

A toggle trigger, as shown in FIG. 12, can be implemented in a variety of ways. Often an optical switch is configured so as to be interrupted once each rotation of the CAM (60) thus creating a stable reference mark. When used in conjunction with a stepper motor, stepping pulses can be counted to determine timing relative to the reference mark.

It is noted that piston pumps can be built that do not utilize cam devices to control piston travel. Cam-less pumps can still take full advantage of this invention.

Figure 11:
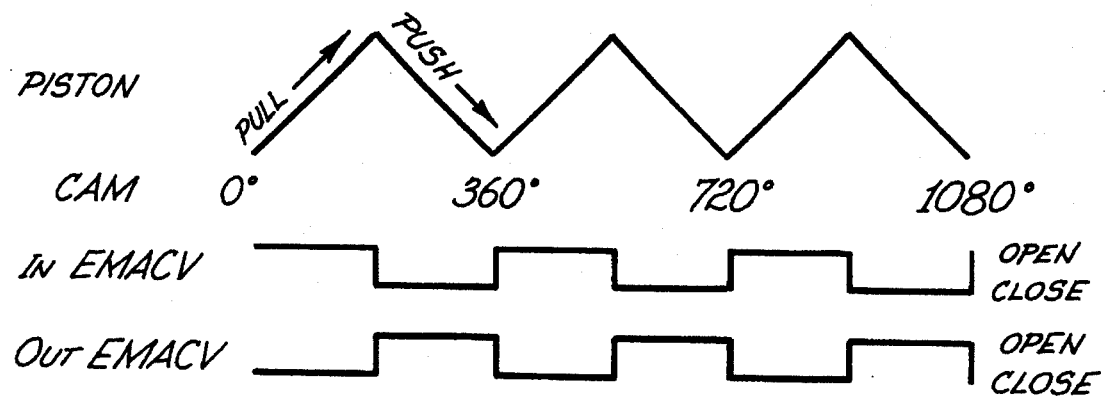
FIG. 11 illustrates, for a typical piston pump, the timing relationship between the opening and closing of both inlet and outlet configured electro-magnetically operated valves.

FIG. 11 illustrates, for a typical piston pump, the timing relationship between: opening and closing of both inlet configuration valves (12) and outlet configuration valves (10) depicted in the 2 bottom traces noted in said fig. as well as pulling and pushing of the piston depicted in the top zig-zag shaped trace. Note that CAM rotation angles are listed in the middle row of the figure. A valve seal member may be configured as a needle would typically be manufactured of a hard material though not limited to thereto, and a valve seat could be made of almost any material, i.e. sapphire, ruby, ceramic, metal plastic, or polymer.

FIG. 12 illustrates a very basic circuit for actuation (opening and closing) of the parent application. When the double pole double throw (DPDT) switch is toggled, current flow through the electro-magnetically actuated valve coil is reversed.

Figure 13:
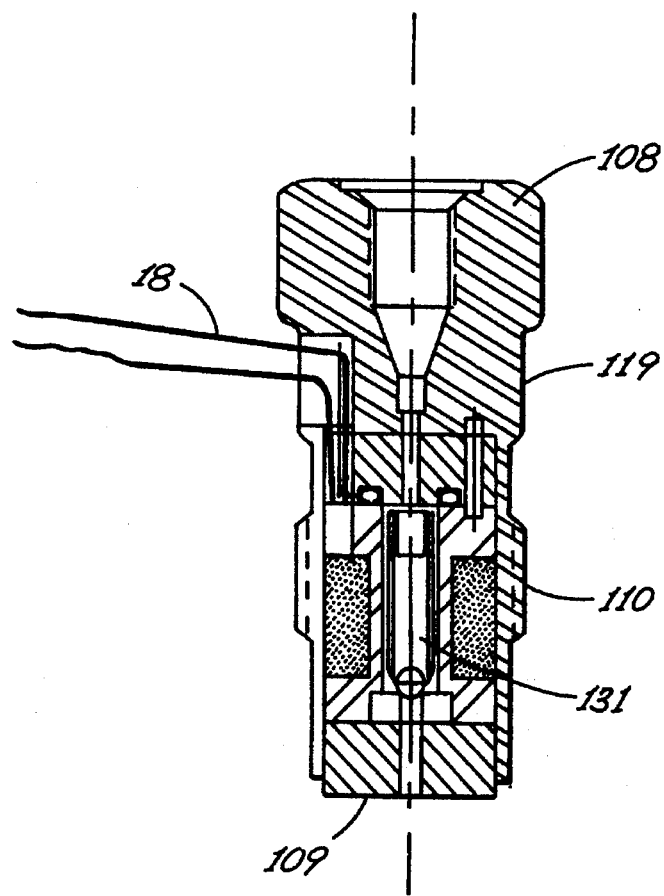
FIG. 13 is a cross-sectional view of an improved electro-magnetically actuated valve embodying the present invention, shown in an outlet valve arrangement.
Figure 14:
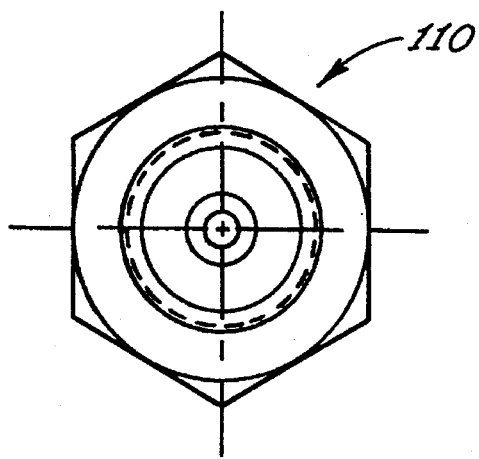
FIG. 14 is an end view of the electro-magnetic actuated valve of FIG. 13.
Figure 15:
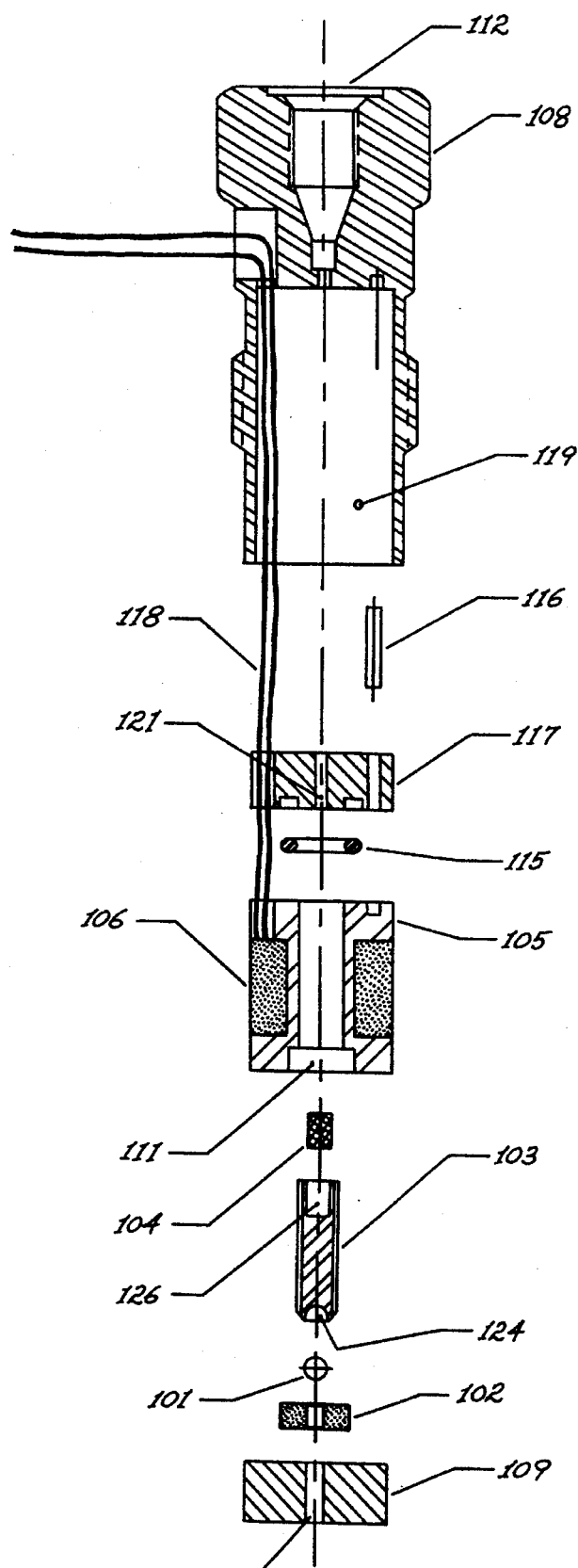
FIG. 15 is a exploded cross sectional view of the electro-magnetically actuated valve of FIG. 13.
Figure 16:
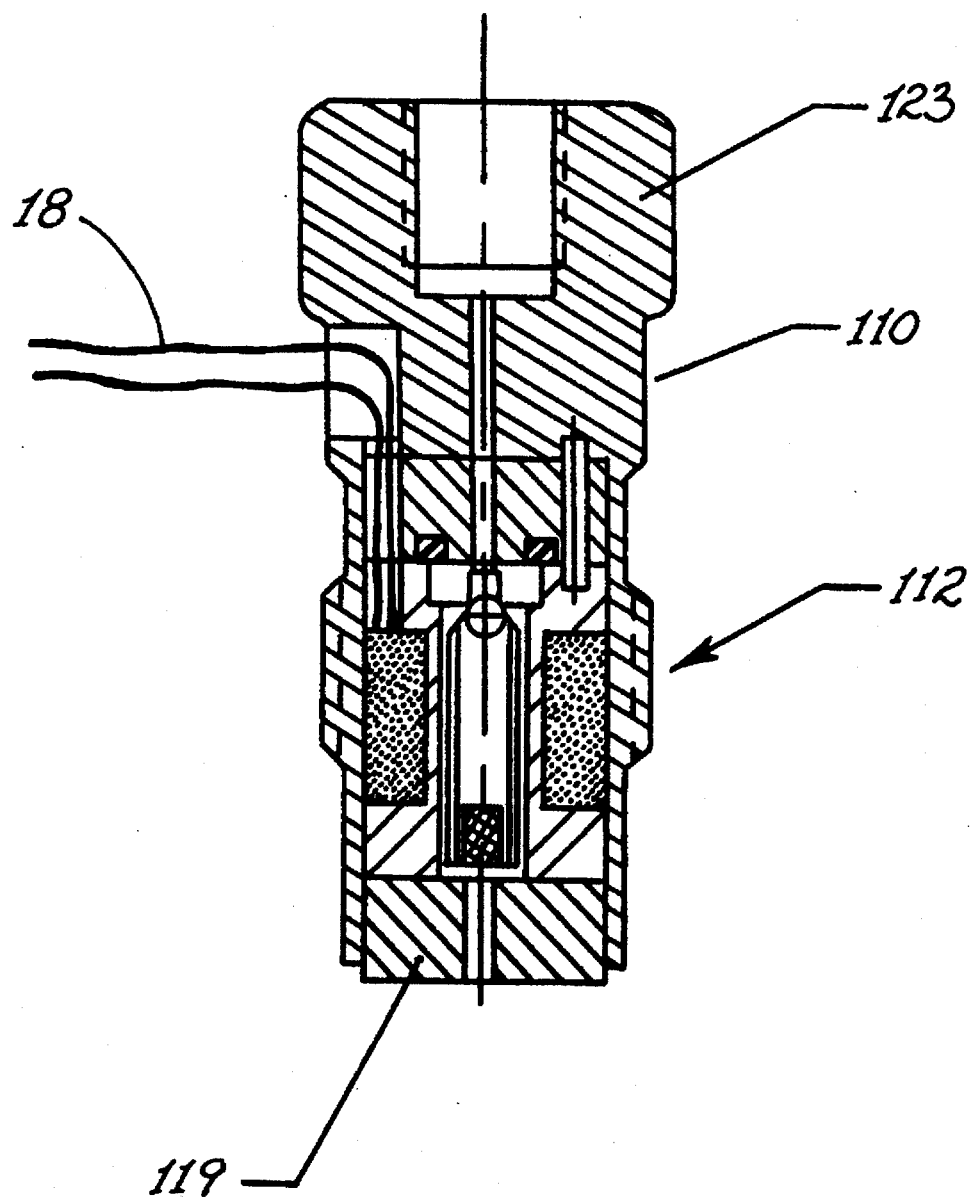
FIG. 16 is a cross sectional view of the electro-magnetically actuated valve of FIG. 13 shown in the inlet arrangement.

With reference to the FIGS. 13 through 25, there is disclosed of the present preferred embodiment of the present invention wherein there is shown an improved electromagnetically actuated valve having an inlet configuration and an outlet configuration wherein FIG. 13 shows that valve as an outlet valve 110 and shown in FIG. 16 as an inlet valve 112.

Referring to FIG. 13 and 15, the preferred embodiment incorporates a bobbin (106) and introduced two new seal plates (109) which (a) seal said bobbin and (b) insulate the magnet (104) from any magnetic attraction to the stainless steel valve body (119) or a pump head of pump 140. Although 316 stainless steel employed in a HPLC component has little magnetic properties, the additional spacing insures that the magnet (104) will not be attracted to the stainless steel, thereby interfering with the performance of the valve; specifically, said magnet is only influenced by the flux field generated by the coil. The bobbin (106) is fabricated from Titanium to further reduce any magnetic interference.

A low pressure seal was added to increase sealing performance as we found a separate seal with a lower durometer required less compression to seal the leak path of the valve. In the preferred embodiment low pressure seal is constructed of an "o" ring (115).

The location of the magnet (104) constructed of Neodymium within coil (105) consisting of a Titanium bobbin and wire wrapped about it's perimeter is now positioned at the very edge of said coil, again to increase the performance of valve operation by providing maximum energy between the magnetic flux field of coil 105 and magnet 104.

We have found that this improved new configuration of the preferred embodiment of said EMACV valve will operate with improvements to pump operation by reducing pressure variations both in the passive mode (i.e. as a standard check valve without energizing coil (105) and with the coil energized. One important element of the improved design is an elongated plunger sub-assembly (131) that is considerably longer than the parent design which provides improved operation due to the increased length to diameter ratio of the plunger reduces the possibility of binding of the plunger on the sides of the bobbin.

Because of problems encountered with certain internal parts consisting of the coil bobbin (105) rotating inside the housing (108), during assembly of said valve into a pump head, with the result that wires (18) become sheared, an anti-rotation locking pin 116 was introduced to prevent rotational movement of said part bobbin (105) relative to housing (108). The pin 116 ties together the bobbin (105), upper seal plate and housing (108). Should lower seal plate washer (109) rotate there is of little concern.

Figure 17:
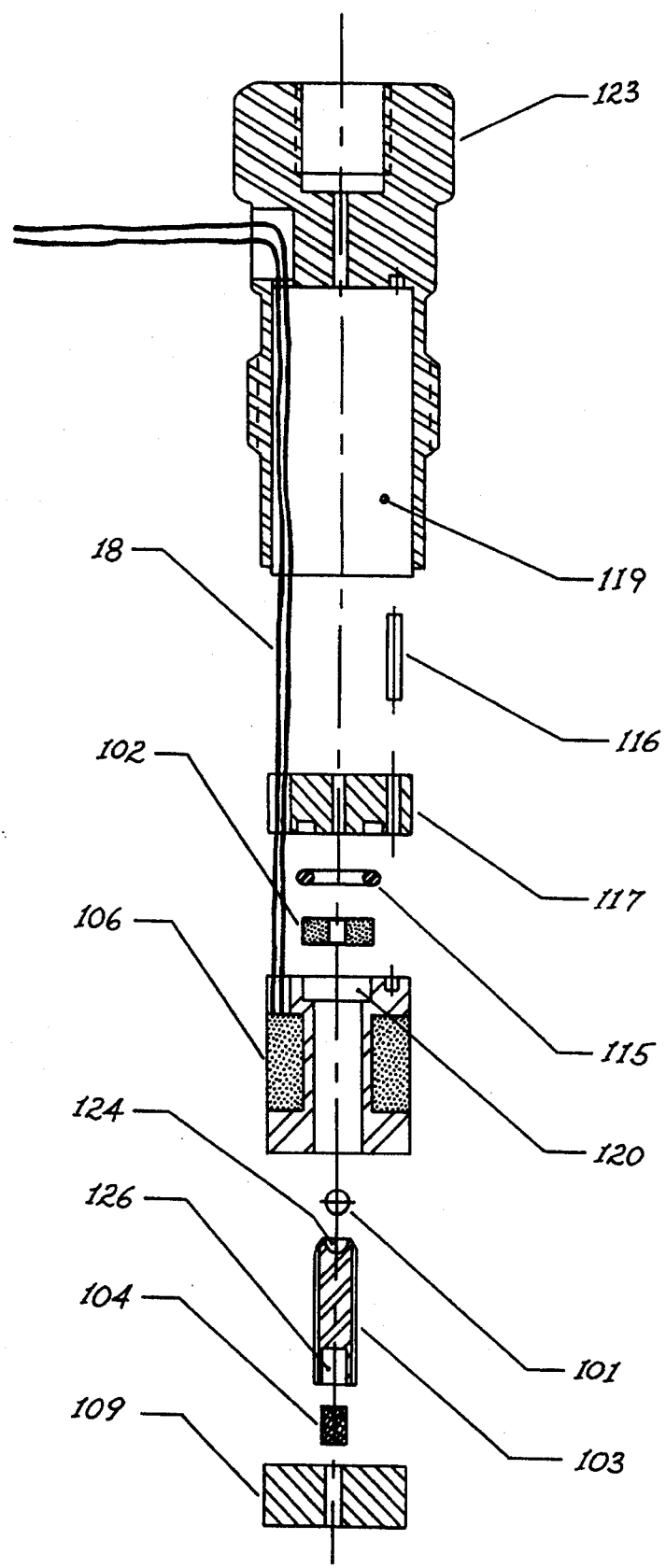
FIG. 17 is an exploded cross sectional view of the electro-magnetically actuated valve of FIG. 16.

Referring to FIG. 16 and FIG. 17, outlet valve 110 includes a housing 123 having an inlet 111 at one end and a hollow cylinder 119 disposed at the opposite end. Coiled bobbin 105 is positioned in said hollow cylinder having an inlet 113 at one end and a tubular chamber 120 at the other end including a fluid conduit 121 extending between said inlet and said tubular chamber.

Figure 18:
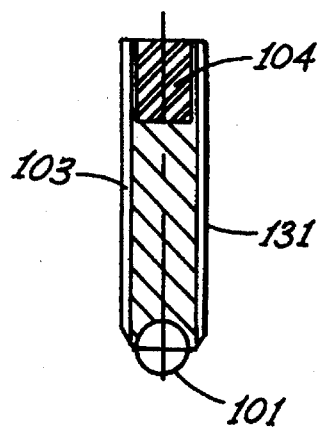
FIG. 18 is a cross sectional view of the plunger sub-assembly of the electro-magnetically actuated valve of FIG. 13.
Figure 19:
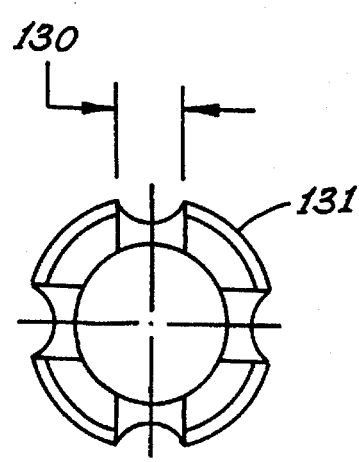
FIG. 19 is an end view of the plunger sub-assembly of FIG. 18 showing grooves to provide flow channels.
Figure 20:
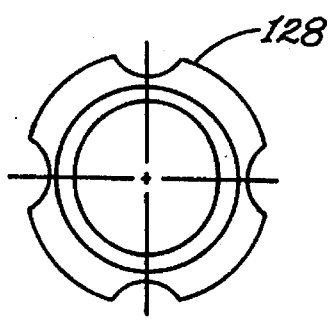
FIG. 20 is an end view of the outlet end of plunger sub-assembly shown in FIG. 18 showing grooves acting as bypass slots.

In the present invention, as is shown in FIG. 18, plunger sub-assembly 131, configured to be moveably positioned in tubular chamber 120 for slidable movement between a first position and a second position therein, includes magnet 104, a valve body seal shown as a ball 101 constructed of non-metallic material. As is shown in FIGS. 19 and 20, sleeve channels 128 extending parallel to the axis of plunger 103 and include bypass slots 130 at the inlet end thereof. As is shown in FIG. 15, the valve body seal is shown as ball 101. It is mounted at one end of plunger 103 and at the opposite end thereof, the magnet 104 is mounted in a recess 126. There is also shown a seal plate 109 provided at the distal end of housing 108 for enclosing tubular chamber 120 and sealing the outlet of the plunger sub-assembly 131.

In the present embodiment, and improved coil 105 is provided in the coil bobbin 105 and is mounted in a recess at the mid-section of the coil bobbin 105 and is connected by a plurality of leads 118 which are connected to a conventional switching apparatus not shown. Said coil is magnetically linked to magnet 104 whereby a magnetic circuit is formed including the moveable plunger subassembly 131 including said magnet and said valve body. Once a magnetic circuit is formed, said electro-magnetically actuated valve is operated by means of the switching apparatus for positively controlling the opening and closing of said valve by passing a current through coil 105 to produce a magnetic field. In this condition, the opened or closed state of said valve is determined by the direction of current flow through said coil which acts on magnet 104 urging valve body seal 101 against seat 102 held in a fixed position in socket 111 by lower seal plate 109 for sealing said valve outlet 114.

In this preferred embodiment, as is shown in FIGS. 18, 19 and 20, plunger 103 is grooved to provide enhanced flow including sleeve channels 128 extending along its entire length and including transverse bypass slots 130 positioned across the inlet face 115 as is shown in FIG. 19. This groove configuration of said plunger is arranged so that liquid passing through said valve can continue to flow even though plunger subassembly 131 is forced up against coil bobbin 105. In the present invention, the location of magnet 104 relative to coil 105 was altered so that the said magnet is now positioned at the very entrance of coil 105 for the purpose of increasing the performance of operation. This change of location of said magnet and coil in the improved valve will now permit running reliably at a passive mode, i.e. as a standard check valve without energizing coil 105. In order to achieve this effect, it was also necessary that plunger 103 by changed to have a considerably longer length than in the parent application.

It is noted, as is shown in FIG. 15, that seat 112, valve body seal 101 and plunger subassembly 131 including plunger 103 including concave carrier at one end and and magnet 104 at the other end may be assembled in reverse order in coil bobbin 105 to provide for an inlet check valve configuration 112. A particularly advantageous feature of the valve of the present invention is that all of the components are readily disassembled or, alternatively, assembled into housing 108 and sealed in place by lower plate seal. In the present invention, when installed in a piston pump, such as shown in the internal parts of the plunger subassembly 131 are in compression to seal against internal leaks. Furthermore, plunger subassembly 131 may be readily removed from housing 108 for cleaning and replacement of component elements contained therein. Referring to FIG. 20, sleeve channels 128 and radial bypass slots 130 are chosen to be large enough so as not to restrict flow through said valve.

In this embodiment of the invention, flow restriction is determined by the inside diameter of associated system tubing and not by the configuration of said sleeve channels or radial bypass slots 130 provided in said plunger subassembly 131 nor is it determined by spacing between valve body seal 101 and associated seat 102.

Figure 21:
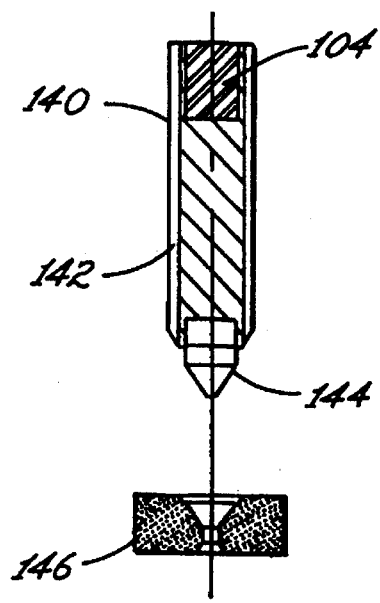
FIG. 21 illustrates an alternate embodiment of plunger sub-assembly of the electro-magnetically actuated valve of the present invention showing a conical body element in an associated conical seat.

Referring to FIG. 21, there is shown an alternate embodiment of a plunger sub-assembly 140 of the electro-magnetically actuated valve of the present invention showing a plunger 142, conical body element 144 in an associated conical seat 146.

Figure 22:
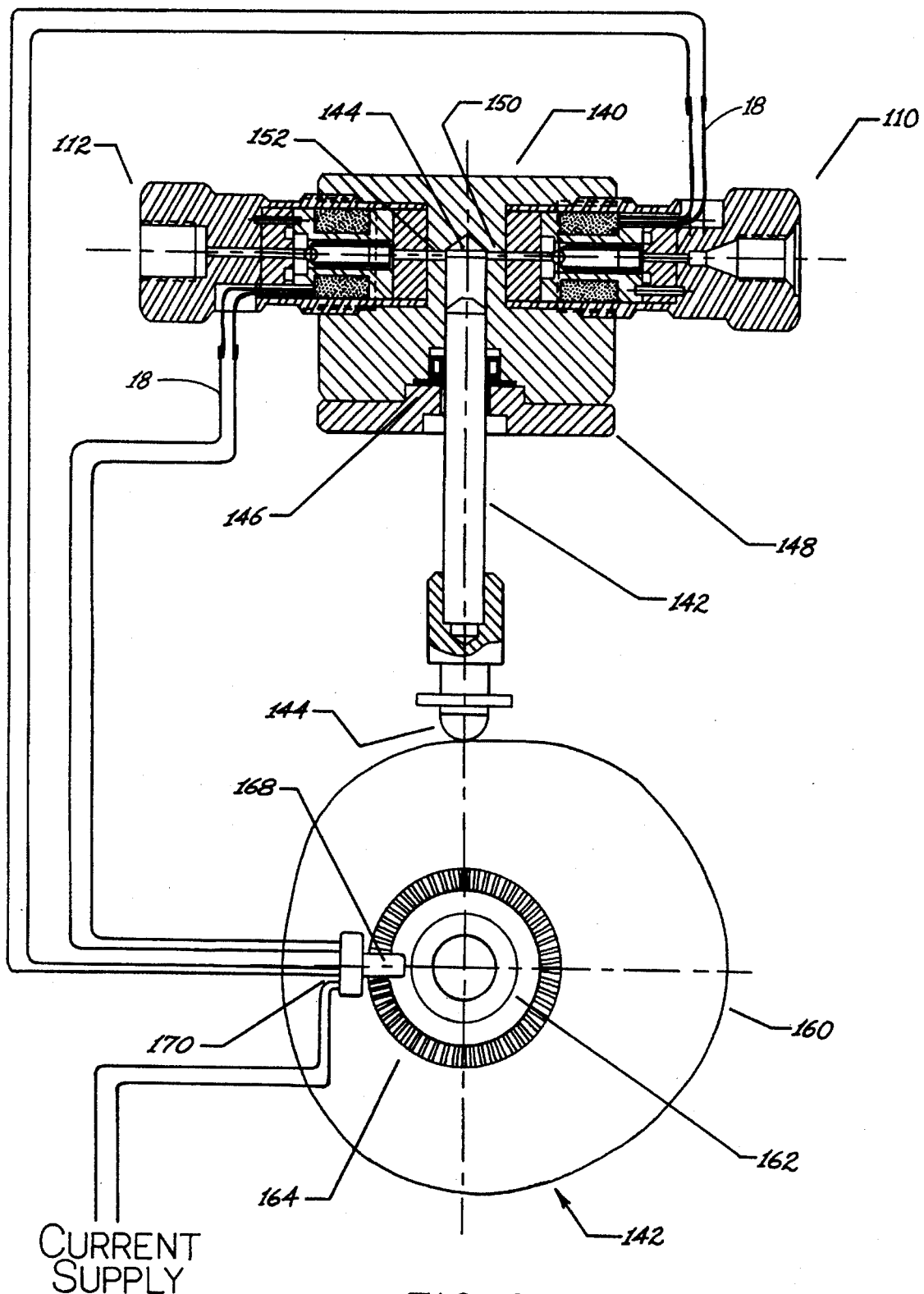
FIG. 22 shows an electro-magnetically operated fluid control system including a pump shown in cross-section employing an outlet valve of FIG. 13 and an inlet valve of FIG. 16 mounted on the pump body and including a electro-optical sensor and optical disk system.

Referring to FIG. 22, there is shown an electro-magnetically operated fluid control system including a pump shown in cross-section employing an outlet valve of FIG. 13 and an inlet valve of FIG. 16 mounted on the pump body and including a electro-optical sensor 142 and optical disk system 162. This system is identical to the system of Figure 10, except the mechanical switch follower 68 and switch 70 with an electro-optical sensor 142 and optical disk 162. As cam 160 turns, the sensor 142 "counts" the make/breaks as they occur as the disk turns. By the count, the pump "knows" where the cam is thus it knows where the piston(s) are. It can then determine when to open or close the appropriate EMACV valve depending on whether the piston is on the pull or push part of the cam curve as shown in FIG. 11.

A possible (conventional) make of an optical sensor would be SY-1R74AY Photo Diode which has both the emitter and receiver built into the single package. It is "U" shaped so as to straddle the rotating disk.

Figure 23:
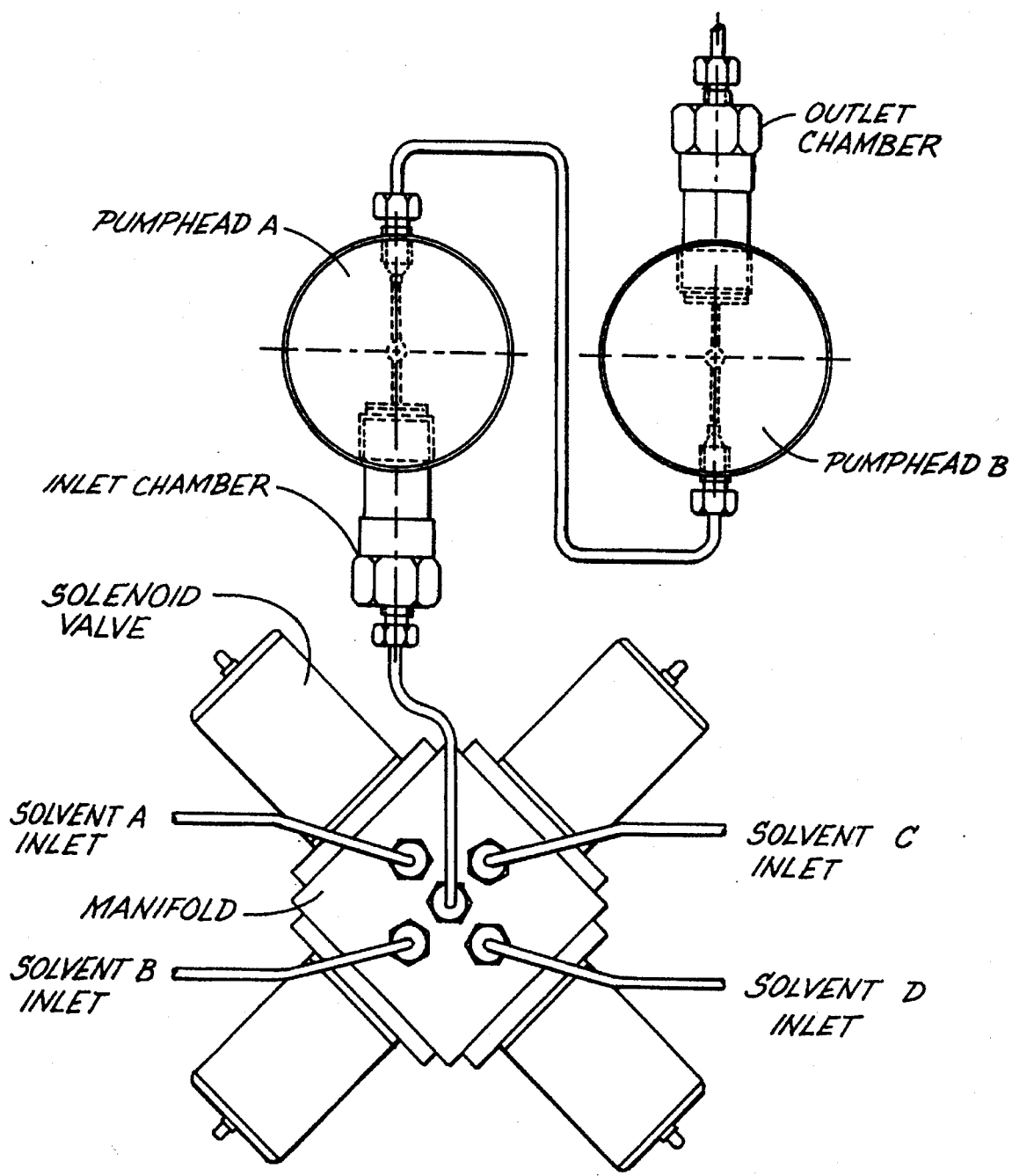
FIG. 23 illustrates a prior art gradient proportioning system using a four valve manifold employing four conventional solenoid-operated valves mounted on a rectangular manifold with four inlets.
Figure 24:
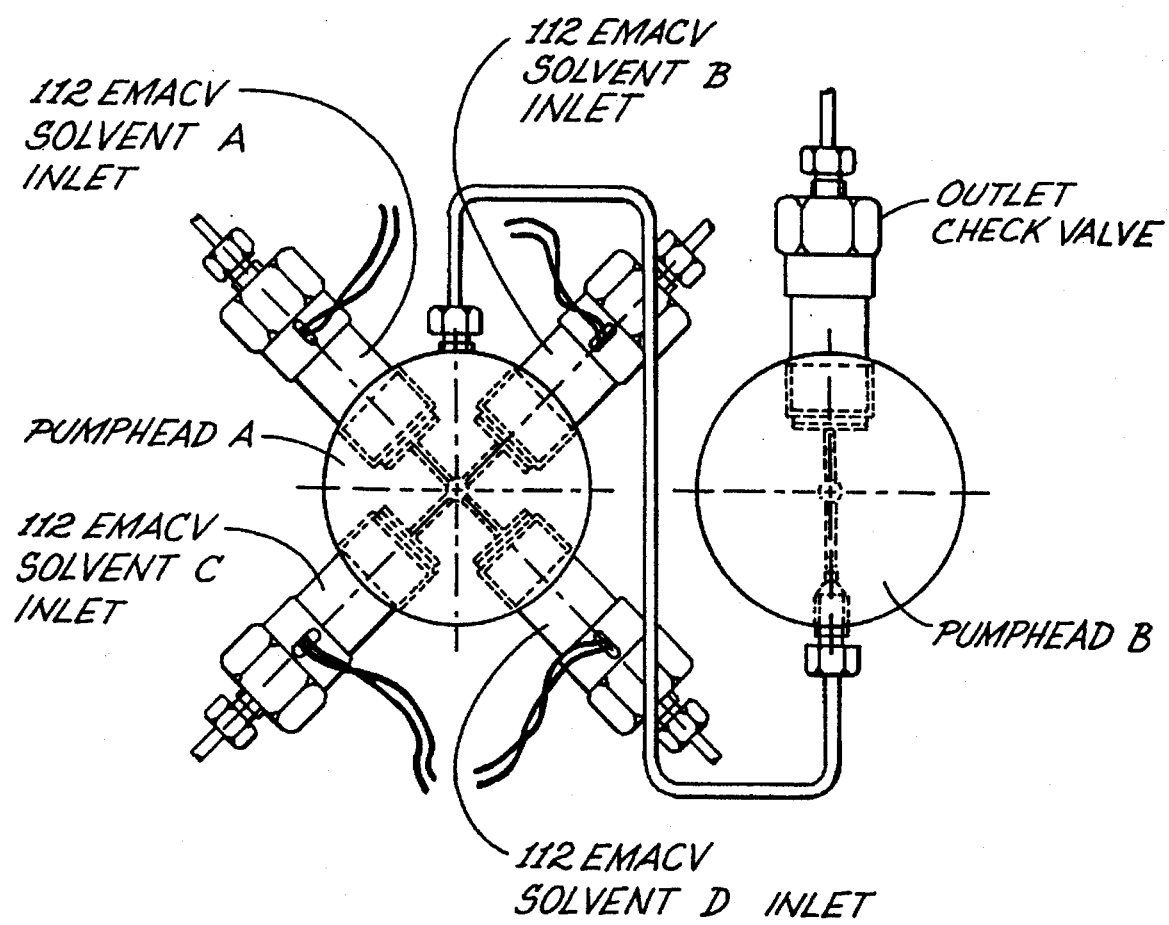
FIG. 24 illustrates an alternate embodiment of the present invention employed in a gradient proportioning system showing a pump head with four electro-magnetic mechanically actuated valves according to the present invention installed radially about the pump head.
Figure 25:
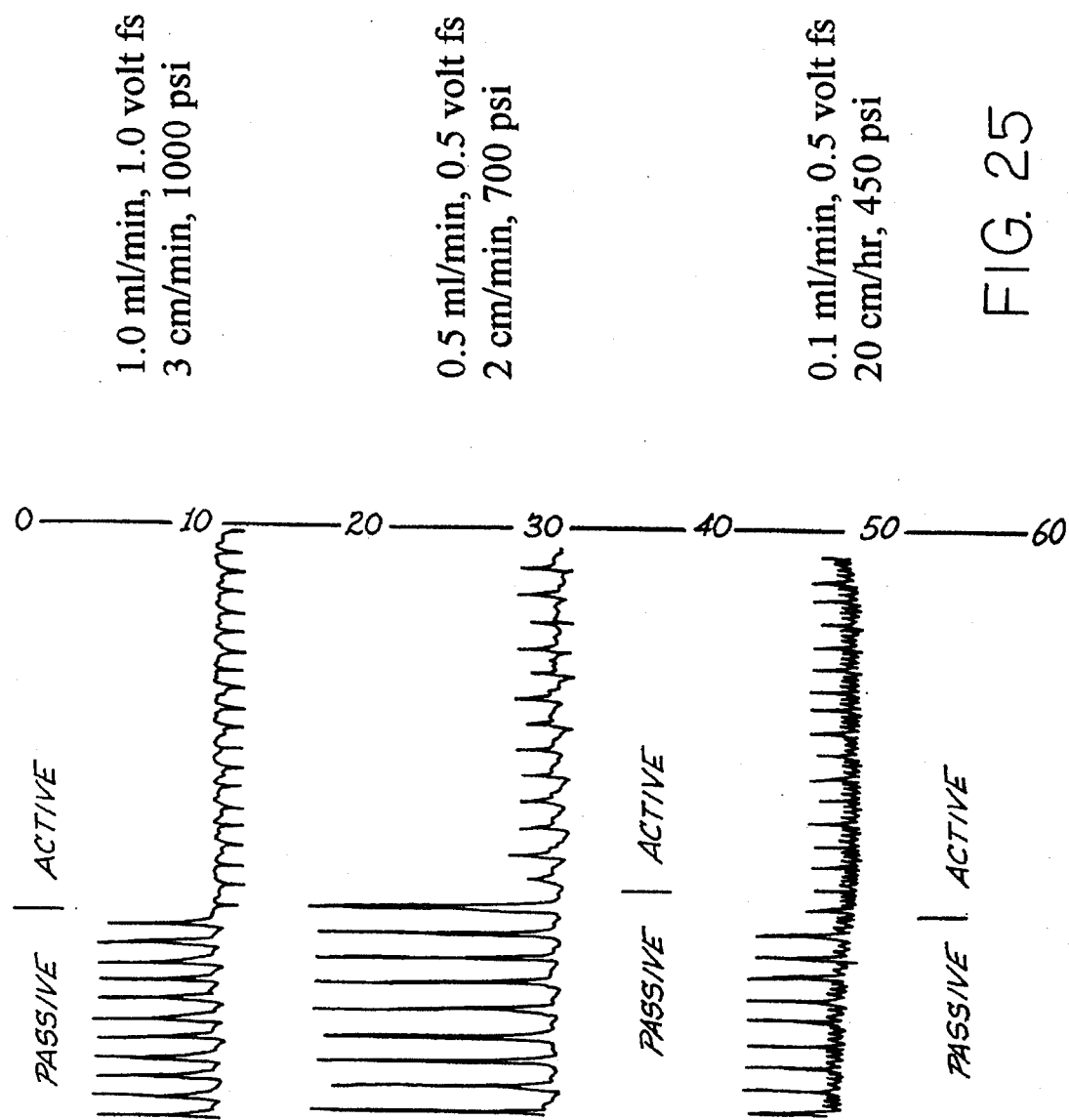
FIG. 25 is a graphic illustration of test results obtained for the present invention as shown in FIG. 13 showing improvements in pressure for different flow rates.

Referring to FIG. 23, there is shown an electro-magnetically operated fluid control system incorporating a HPLC pump configured to run on four different solvents at the same time which is known in the art as a gradient system. In such a system, the four solvents are usually metered at different volumes making up a gradient proportioning run. As is shown in the FIG., the metering of solvents is accomplished by four electro-magnetically operated valves of the present invention which can be controlled as to the amount of time they are opened or closed. As is shown in the FIG. 23, four electro-magnetically valves according to the present invention are mounted directly onto the manifold which will serve not only as an inlet check valve but also as a gradient proportioning valve.

What is claimed is:

1. An electro-magnetically operated valve for control of pressurized fluid comprising:
 a) valve body means having a first side and a second side comprising:
   i) a housing having an opening at one end and a hollow cylinder at the other—end—;
   ii) a bobbin means for positioning an electro-magnetic coil inside the valve body means disposed in the hollow cylinder having a fixed valve seat disposed at—one—end, a tubular chamber disposed at—the other end—and—a fluid conduit extending therebetween having an inlet and an outlet;

b) a plunger subassembly movably mounted in said tubular chamber for movement between a first opened position and a second sealed position—, said subassembly—comprising a plunger of cylindrical construction having external flow passage means and including a magnet disposed in one end and a valve seal means disposed in the other end operative between a open state and a closed state for opening and closing said fluid conduit and thereby regulate flow of fluid through the valve body means end for regulating flow of fluid through the valve body means by alternatively permitting and preventing flow there through;

c) sensor means for sensing phase relations of a piston of a pump connected to the valve body means for timing opening and closing of said valve;

d) control means—connected to—the bobbin means operationally connected to a switch apparatus for forming a magnetic circuit with the magnet for operationally urging the plunger subassembly between the first open position to the seconded sealed position by passing a current through said coil, the opened or closed state of the valve seal means being determined by the direction of current flow through said coil, the opened or closed state of the seal means being determined by the directions of current flow through said coil acting on said magnet tending to urge the valve seal means alternatively against the valve seat for sealing the outlet or away from said valve seat for opening the valve seal means.

2. The valve of claim 1 wherein the valve body means is configured as an outlet valve for use with a pump where the first side is an inlet and the second side is an outlet for the fluid conduit.

3. The valve of claim 1 wherein the valve body means is configured as an inlet valve for use with a pump where the first side is an outlet end and the second side is an inlet end of said fluid conduit.

4. The valve of claim 1 wherein the valve seal means comprises a ball.

5. The valve of claim 1 wherein fluid is negatively pressurized as in a suction phase of pumping.

6. The valve of claim 1 wherein the valve seal means comprises a ball valve that operates to urge the ball into the valve seat with sufficient force to resist opening against liquid or gas pressure and so acts as an active opened—closed valve.

7. The valve as claimed in claim 1 wherein the bobbin, the plunger, and valve seal means are fabricated from materials with high chemical resistance and—in particular—employs a conical valve seal means.

8. The valve as claimed in claim 5 wherein the pump is connected in a system for high performance liquid chromatography (HPLC).

9. The valve as claimed in claim 5 wherein the pump is connected in a system for capillary electrophoresis (CE).

10. The valve as claimed in claim 5 wherein the pump is connected in a system for mass spectrometry (MS).

11. The valve as claimed in claim 1 which does not rely on gravity to be operated and therefore is operable in any position including a horizontal arrangement wherein the fluid conduit horizontally arranged—in—a system for mass spectrometry (MS).

12. A system for high performance liquid chromatography (HPLC) comprising electro-magnetically operated valve means comprising an inlet valve and an outlet valve including;

a) valve body means having a first side and a second side comprising:
 i) a housing having an opening at one end and a hollow cylinder at the other—end—;
 ii) a bobbin means for positioning an electro-magnetic coil inside the valve body means disposed in the hollow cylinder having a one end and other end having a fixed valve seat disposed at the other end, a tubular chamber disposed at the other end defining a fluid conduit extending therebetween having an inlet and an outlet;

b) a plunger subassembly movably mounted in said tubular chamber for movement between a first opened position and a second sealed position comprising a plunger of cylindrical construction having external flow passage means and including a magnet disposed in one end and a valve seal means disposed in the other end operative between a open state and a closed state for opening and closing said fluid conduit and thereby regulate flow of fluid through the valve body means end for regulating flow of fluid through the valve body means by alternatively permitting and preventing flow there through;

c) sensor means for sensing phase relations of a piston of a pump connected to the valve body means for timing opening and closing of said valve;

d) control means —connected to—the bobbin means operationally connected to a switch apparatus for forming a magnetic circuit with the magnet for operationally urging the plunger subassembly between the first open position to the seconded sealed position by passing a current through said coil, the opened or closed state of the valve seal means being determined by the direction of current flow through said coil, the opened or closed state of the seal means being determined by the directions of current flow through said coil acting on said magnet tending to urge the valve seal means alternatively against the valve seat for sealing the outlet or away from said valve seat for opening the valve seal means wherein said valves are mounted in a pump body including a CAM operated control system comprising.

13. A gradient system for mixing a plurality of solvents comprising electro-magnetically operated valve means comprising an four inlet valves, each valve including;

a) valve body means having a first side and a second side comprising:
 i) a housing having an opening at one end and a hollow cylinder at the other;
 ii) a bobbin means for positioning an electro-magnetic coil inside the valve body means disposed in the hollow cylinder having a one end and other end having a fixed valve seat disposed at the other end, a tubular chamber disposed at the other end defining a fluid conduit actually extending therebetween having an inlet and an outlet (SP);

b) a plunger subassembly movably mounted in said tubular chamber for movement between a first opened position and a second sealed position comprising a plunger of cylindrical construction having external flow passage means and including a magnet disposed in one end and a valve seal means disposed in the other end operative between a open state and a closed state for opening and closing said fluid conduit and thereby regulate flow of fluid through the valve body means end for regulating flow of fluid through the valve body means by alternatively permitting and preventing flow there through;

c) sensor means for sensing phase relations of a piston of a pump connected to the valve body means for timing opening and closing of said valve;

d) control means—connected to—the bobbin means operationally connected to a switch apparatus for a magnetic circuit with the magnet for operationally urging the plunger subassembly between the first open position to the seconded sealed position by passing a current through said coil, the opened or closed state of the valve seal means being determined by the direction of current flow through said coil, the opened or closed state of the seal means being determined by the directions of current flow through said coil acting on said magnet tending to urge the valve seal means alternatively against the valve seat for sealing the outlet or away from said valve seat for opening the valve seal means wherein said valves are mounted in a pump body including a CAM operated control system.

14. The gradient system of claim 13 wherein a plurality of electro-magnetically operated valves are mounted on a pump as combination proportioning and inlet valves such that said valves open during a suction stroke so as to effect proportioning and mixing of solvents flowing into each valve.

* * * * *